United States Patent [19]

Rothenberg et al.

[11] Patent Number: 5,020,543

[45] Date of Patent: Jun. 4, 1991

[54] VENOUS ACCESS CATHETER FOR REMOVING A CULTURE

[76] Inventors: Robert E. Rothenberg, 35 Sutton Pl., New York, N.Y. 10022; Raymond D. LaRaja, 3 Beechwood Rd., Bronxville, N.Y. 10708; John W. Odom, 2100 Linwood Ave., Apt. 6N, FortLee, N.J. 07024

[21] Appl. No.: 431,651

[22] Filed: Nov. 3, 1989

[51] Int. Cl.$^5$ .............................................. A61B 5/00
[52] U.S. Cl. ................................. 128/760; 128/749; 604/43; 604/167
[58] Field of Search ............................. 128/749–750, 128/756, 760, 765–766, 768; 604/30, 35–38, 43, 52–53, 164, 167, 169, 173, 181, 280

[56] References Cited

U.S. PATENT DOCUMENTS

| | | | |
|---|---|---|---|
| 2,767,703 | 10/1956 | Niebuigs | 128/749 |
| 3,777,743 | 12/1973 | Binard et al. | 128/305 |
| 3,800,781 | 4/1974 | Zalucki | 128/304 |
| 3,995,623 | 12/1976 | Blake et al. | 128/768 X |
| 4,072,146 | 2/1978 | Howes | 128/768 X |
| 4,131,112 | 12/1978 | Kopito et al. | 128/765 |
| 4,235,244 | 11/1980 | Abele et al. | 128/749 |
| 4,457,313 | 7/1984 | Alter | 128/759 |
| 4,496,347 | 1/1985 | MacLean et al. | 604/164 |
| 4,534,362 | 8/1985 | Schumacher et al. | 128/738 |
| 4,601,701 | 7/1986 | Mueller, Jr. | 604/83 |
| 4,653,510 | 3/1987 | Koll | 128/756 |
| 4,660,570 | 4/1987 | Dombrowski | 128/765 |
| 4,662,381 | 5/1987 | Inaba | 128/756 |
| 4,756,708 | 7/1988 | Martin | 604/93 |
| 4,808,155 | 2/1989 | Mahurkar | 604/43 |
| 4,850,373 | 7/1989 | Zatloukal et al. | 128/749 |

OTHER PUBLICATIONS

Stan Markus, M. D. and Stephen Buday, M. D.: Culturing Indwelling Central Venous Catheters In Situ, Infections in Surgery May, 1989, pp. 157–162.

Primary Examiner—Max Hindenburg
Attorney, Agent, or Firm—John P. White

[57] ABSTRACT

An improved catheter is provided comprising a flexible cannula having at least two lumens formed in the entire length of the cannula. A plug seals one end of one of the lumens. One end of a filament is connected to the underside of the plug and the filament extends through the entire length of the lumen. The plug is configured such that by pulling on the other end of the filament the plug is pulled through the lumen to thereby extract a culture sample when the catheter is implanted. A culture sample can be taken to detect the possibility of catheter sepsis, without the need to remove the catheter.

19 Claims, 1 Drawing Sheet

VENOUS ACCESS CATHETER FOR REMOVING A CULTURE

BACKGROUND OF THE INVENTION

The present invention is directed to an improved venous access catheter and more particularly to a catheter having means for obtaining a culture sample without removal of the catheter.

In the past few years there has developed a great increase in the need for and usage of indwelling central venous catheters. Although there are obvious benefits of these devices in supplying access for total parenteral nutrition and for administration of various medications, several serious complications have been noted in their use. The most significant problem encountered in their prolonged use has been the tendency for the catheters to become colonized with bacteria or yeast, thus producing so-called "catheter sepsis".

Several solutions have been devised for the early diagnosis of catheter infection and its differentiation from other causes of sepsis. Unfortunately, most clinicians find it necessary to remove a catheter when it is suspected of harboring infection. The removal of a catheter in order to determine the existence of infection requires the insertion of a new catheter, thereby inviting the possibility of introducing new bacteria or a complication attendant upon its reinsertion into the subclavian or internal jugular veins. It would therefore be advantageous to provide an arrangement to permit cultures to be taken without the need for catheter removal or the fear of introducing bacteria from the outside.

SUMMARY OF THE INVENTION

In accordance with the present invention a catheter is provided comprising a flexible cannula having at least two lumens formed in the length of the cannula. Plug means are provided for sealing one end of one of the lumens. Filament means having two ends are provided, with one end connected to the plug means, and said filament means extending through the length of the one lumen. The plug means is configured such that by pulling the other end of the filament means, the seal is unsealed and the plug means is pulled through the lumen to extract a culture sample, whereby a culture sample may be extracted through the catheter when the catheter is implanted without removal of the catheter.

Preferably, the cannula would have three lumens with one of the lumens initially sealed with the plug means, which would be in the form of a semi-flexible circularly shaped diaphragm to thereby seal the lumen. This lumen will remain sealed and sterile until the need to rule out infection occurs. At that time, the diaphragm and filament would be withdrawn and cultures would be taken. The lumen from which the diaphragm and filament have been withdrawn would then be used as an extra access lumen should the culture prove to be negative. The new catheter according to the invention would thus obviate the dangers and costly practice of removing a central venous line catheter unnecessarily.

In accordance with another aspect of the invention a culture sample device is provided for use with a catheter having at least one lumen defined in a cannula. The culture sample device comprises filament means having two ends, and brush means formed at one end of the filament means, said brush means being radially dimensioned to be received inside said lumen, whereby a culture sample may be extracted through the catheter when the catheter is implanted without removal of the catheter. These and other advantages of the present invention will become apparent with reference to the following description and drawings.

DESCRIPTION OF THE PREFERRED EMBODIMENT

Figure 1:
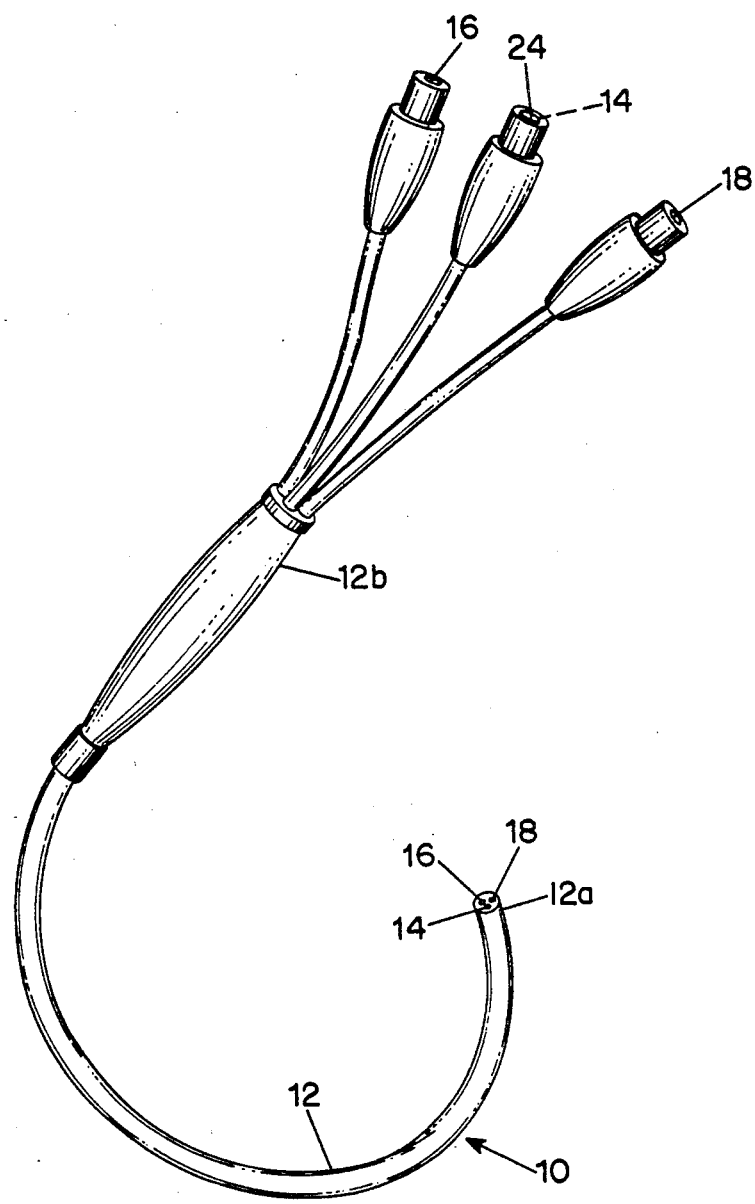
FIG. 1 is a perspective view of a three lumen catheter according to the invention.

According to the present invention a catheter is provided comprising a flexible cannula having at least two lumens formed in the length of the cannula, plug means for sealing one end of one of the lumens, filament means having two ends with one end connected to the plug means, said filament means extending through the length of the one lumen. The plug means is configured such that by pulling the other end of the filament means, the seal is unsealed and the plug means is pulled through the one lumen to extract a culture sample, whereby a culture sample may be extracted through the catheter when the catheter is implanted without removal of the catheter.

Preferably the cannula has three lumens and the plug means comprises a semiflexible circularly shaped diaphragm. The filament means may comprise a braided two strand filament or a single strand filament, with the strands being made of wire or plastic. The filament is attached to the underside of the plug means at the center of the plug. A second plug means is preferably provided to seal the other end of the one lumen, and wherein the other end of the filament means is attached to the second plug means. The cannula may be about 25 cm long and about 4 mm in diameter, with each lumen having a diameter of about 1 mm. The plug means may be in the form of a flexible disc and may have a diameter of about 1.5 mm with the filament means having a diameter of about 0.6 mm.

According to another aspect of the invention, a culture sample device for use with a catheter having at least one lumen defined in a cannula is provided comprising plug means for sealing one end of the lumen, and filament means having two ends, one end being connected to the plug means and wherein said filament means extends the entire length of the lumen. The plug means is configured such that by pulling the other end of the filament means, the seal is unsealed and the plug means is pulled through the lumen to extract a culture sample, whereby a culture sample may be extracted through the catheter when the catheter is implanted without removal of the catheter.

In accordance with another aspect of the invention a culture sample device is provided for use with a catheter having at least one lumen defined in a cannula. The culture sample device comprises filament means having two ends, and brush means formed at one end of the filament means, said brush means being radially dimensioned to be received inside said lumen, whereby a culture sample may be extracted through the catheter when the catheter is implanted without removal of the catheter.

The device preferably has a plug formed at the one end of the filament means such that the brush means is displaced from the one end of the filament means. The plug means preferably seals one end of the lumen (the end to be implanted). The plug means is configured such that by pulling the other end of the filament means, the seal is unsealed and the plug means and brush means are pulled through the lumen to extract a culture sample. The culture sample device may be provided with a catheter having one or more lumens defined in a cannula.

Referring now to the figures, a catheter 10 according to the invention comprises a cannula 12 having three lumens 14, 16 and 18 defined longitudinally through the entire length of the cannula 12. One of the lumens 14 is initially sealed at the so-called implanted end 12a of the cannula by way of a semiflexible diaphragm or disk 20 having a diameter slightly larger than the diameter of the lumen 14. Attached to the underside of the disk 20 is a braided filament 22 which is attached centrally to the plug 20 and extends the entire length of the lumen 14 to the other, non-implanted end 12b of the catheter, where the filament 22 is connected to another plug 24 which seals the non-implanted end of the lumen in the same manner as the implanted end.

In use, the end 12a of the catheter is implanted and provides two working lumens 16 and 18, with the other lumen 14 initially sealed. When a culture sample is desired, the plug 24 at the non-implanted end is detached from the lumen and pulled so that the filament 22 pulls plug 20 through the lumen 14 in a manner like an inside-out umbrella to thereby extract a culture sample.

The sample is then analyzed to determine whether the implanted area has become colonized with bacteria or yeast, otherwise known as catheter sepsis. If the culture proves to be negative, the third lumen 14 can serve as an additional lumen, thus obviating the removal of the entire catheter. If the culture proves to be positive, the catheter may then be entirely removed and later replaced.

Figure 3:
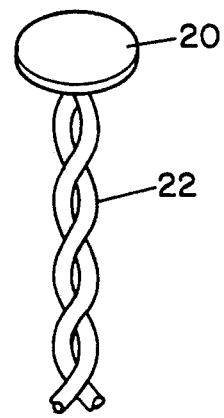
FIG. 3 is a perspective view of the flexible diaphragm plug with attached filament according to the invention.
Figure 4:
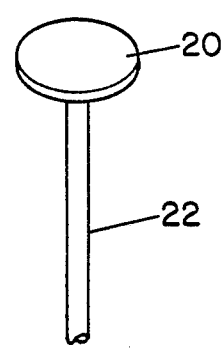
FIG. 4 is a variation of a flexible plug and single filament according to the invention.

Shown in FIG. 3 is the disk plug 20 attached to filament 22. The filament may be a two-strand arrangement as shown in FIG. 3 or a single strand configuration as shown in FIG. 4. In either case, the strand may be made of wire or plastic. The plug 20 is initially sealed to the implanted end of the catheter 12a in a manner well known to those skilled in the art. The breakaway force of this initial seal is selected so that the seal remains intact during normal use, but is easily unsealed during pulling of the filament from the non-implanted end 12b of the catheter. The plug 24 is likewise sealed at the non-implanted end in a similar manner.

Figure 2:
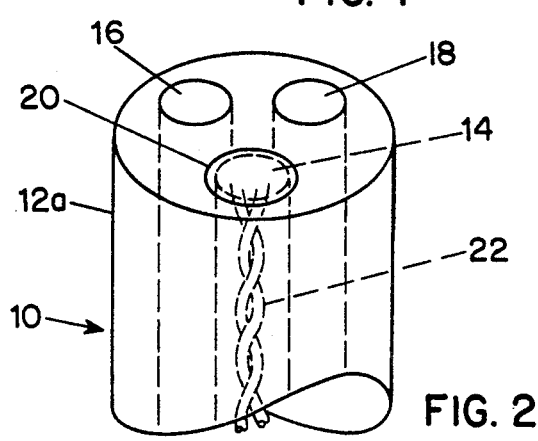
FIG. 2 is an enlarged view of part of the catheter shown in FIG. 1, showing the end of the catheter intended to be implanted.
Figure 5:
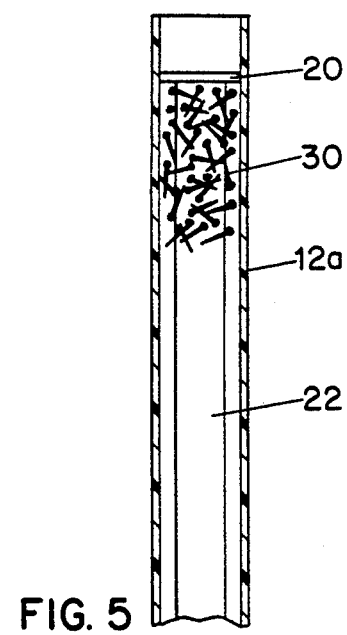
FIG. 5 is a perspective view of a culture sample device having brush means.

Shown in FIG. 5 is a perspective view of a modified culture sample device according to the invention wherein brush fibers 30 are provided at the end of the filament 22 displaced from the one end of the filament. A plug 20 is also shown. This device may, like the device shown in FIGS. 2–4, be provided inside a lumen of a single or multiple lumen catheter, with the plug 20 initially sealing the end of the lumen, as in FIG. 2. The seal may be unsealed by pulling the filament 22 at its other, non-implanted end, and then a culture may be obtained by pushing the filament so that the plug and brush fibers extend out of the lumen, and then pulling the filament to extract the sample on the brush fibers 30. The culture sample device according to FIG. 5 need not be initially provided in a catheter when the catheter is implanted. The device may thus be inserted later, through the non-implanted end.

Although a preferred embodiment of the invention has been shown and described, it will become apparent to those skilled in the art that additions, modifications, substitutions and omissions may be made in the disclosed catheter without departing from the spirit or scope of the invention. Such modifications and the like are within the scope of the invention, as defined in the appended claims.

What is claimed is:

1. A catheter for administering or removing fluids, and for extracting a culture sample, comprising;
   a flexible cannula having at least two lumens formed in the length of the cannula;
   plug means for providing a seal for sealing one end of one of the lumens, to thereby seal the one lumen until a culture sample is desired, flexible filament means having two ends with one end connected to the plug means, said filament means extending through the length of the one lumen, said plug means being configured such that by pulling the other end of filament means, the seal of the plug means with the one lumen is broken and the plug means is pulled through the one lumen to extract a culture sample, whereby a culture sample may be extracted through the one lumen in the catheter when the catheter is implanted without removal of the catheter, the one lumen also providing an additional access or collection lumen after the culture sample is extracted.

2. The catheter according to claim 1, wherein the cannula has three lumens.

3. The catheter according to claim 1, wherein the plug means comprises a flexible circularly shaped diaphragm.

4. The catheter according to claim 1, wherein the filament means comprises a braided filament formed of two strands.

5. The catheter according to claim 1, wherein the filament means comprises a single strand.

6. The catheter according to claim 1, wherein the filament means is made of wire.

7. The catheter according to claim 1, wherein the filament means is made of plastic.

8. The catheter according to claim 1, wherein the one end of the filament means is attached to the underside of the plug means at its center.

9. The catheter according to claim 1, wherein a second plug means is provided to seal the other end of the lumen, and wherein the other end of the filament means is attached to the second plug means.

10. The catheter according to claim 1, wherein the cannula is about 25 cm long and about 4 mm in diameter, and wherein each lumen has a diameter of about 1 mm, and wherein the plug means has a diameter of about 1.5 mm and the filament means has a diameter of about 0.6 mm.

11. A culture sample device for use with a flexible catheter having at least two lumens defined in a cannula comprising:
   plug means for providing a seal for sealing one end of one of the lumens to thereby seal the one lumen until a culture sample is desired;

flexible filament means having two ends, one end being connected to the plug means and wherein said filament means extends the entire length of the one lumen, said plug means being configured such that by pulling the other end of the filament means, the seal of the plug means with the one lumen is broken and the plug means is pulled through the one lumen to extract a culture sample, whereby a culture sample may be extracted through the one lumen in the catheter when the catheter is implanted without removal of the catheter, the one lumen also providing an additional access or collection lumen after the culture sample is extracted.

12. The culture sample device according to claim 11, wherein the plug means comprises a flexible circularly shaped diaphragm.

13. The culture sample device according to claim 11, wherein the filament means comprises a braided filament formed of two strands.

14. The culture sample device according to claim 11, wherein the filament means comprises a single strand.

15. The culture sample device according to claim 11, wherein the filament means is made of wire.

16. The culture sample device according to claim 11, wherein the filament means is made of plastic.

17. A culture sample device for use with a flexible catheter having at least two lumens defined in a cannula comprising:

flexible filament means having two ends, and brush means and a plug means formed at one end of the filament means for providing a seal for sealing one end of one of the lumens to thereby seal the one lumen until a culture sample is desired, wherein the brush means is displaced from the one end of the filament means and wherein the plug means seals one end of the one lumen, said brush means being radially dimensioned to be received inside said one lumen, and said plug means being configured such that by pulling the other end of the filament means, the seal of the plug means with the one lumen is broken and the plug means and brush means are pulled through the one lumen to extract a culture sample, whereby a culture sample may be extracted through the one lumen in the catheter when the catheter is implanted without removal of the catheter, the one lumen also providing an additional access or collection lumen after the culture sample is extracted.

18. The culture sample device according to claim 17, further comprising a catheter having at least one lumen defined in a cannula.

19. The culture sample device according to claim 18, wherein the catheter has at least two lumens defined in the cannula.

* * * * *